United States Patent [19]
Parekh

[11] Patent Number: 5,266,241
[45] Date of Patent: Nov. 30, 1993

[54] HAPTIC ATTACHMENT FOR SOFT INTRAOCULAR LENS

[75] Inventor: Ramesh V. Parekh, Irvine, Calif.

[73] Assignee: Iolab Corporation, Claremont, Calif.

[21] Appl. No.: 834,458

[22] Filed: Feb. 12, 1992

[51] Int. Cl.⁵ ............................................. B29D 11/00
[52] U.S. Cl. ..................................... 264/1.7; 264/2.7; 425/808; 623/6
[58] Field of Search ................ 264/1.4, 1.7, 261, 325, 264/2.7, 1.1; 623/6; 425/808; 65/23

[56] References Cited

U.S. PATENT DOCUMENTS

| | | | |
|---|---|---|---|
| 4,015,965 | 4/1977 | Deeg et al. | 65/23 |
| 4,068,933 | 1/1978 | Siederman | 264/1.4 |
| 4,786,445 | 11/1988 | Portnoy | 264/1.4 |
| 4,880,426 | 11/1989 | Ting et al. | 623/6 |
| 4,894,062 | 1/1990 | Knight et al. | 623/6 |
| 4,936,849 | 6/1990 | Knoll et al. | 623/6 |

FOREIGN PATENT DOCUMENTS

WO90/04512  5/1990  World Int. Prop. O.

Primary Examiner—Jeffery Thurlow
Assistant Examiner—Mathieu Vargot
Attorney, Agent, or Firm—Joel R. Petrow

[57] ABSTRACT

A method of molding a deformable optic for a soft intraocular lens in which the optic has an opening therein for securely receiving a filamentary fixation member is disclosed. The method includes positioning a wire-like insert member in a mold for the optic at a location corresponding to the desired location of the opening, filling the mold about the wire-like insert member with a curable material selected to form the deformable optic, curing the material, and removing the wire-like insert member from the cured, molded optic.

13 Claims, 4 Drawing Sheets

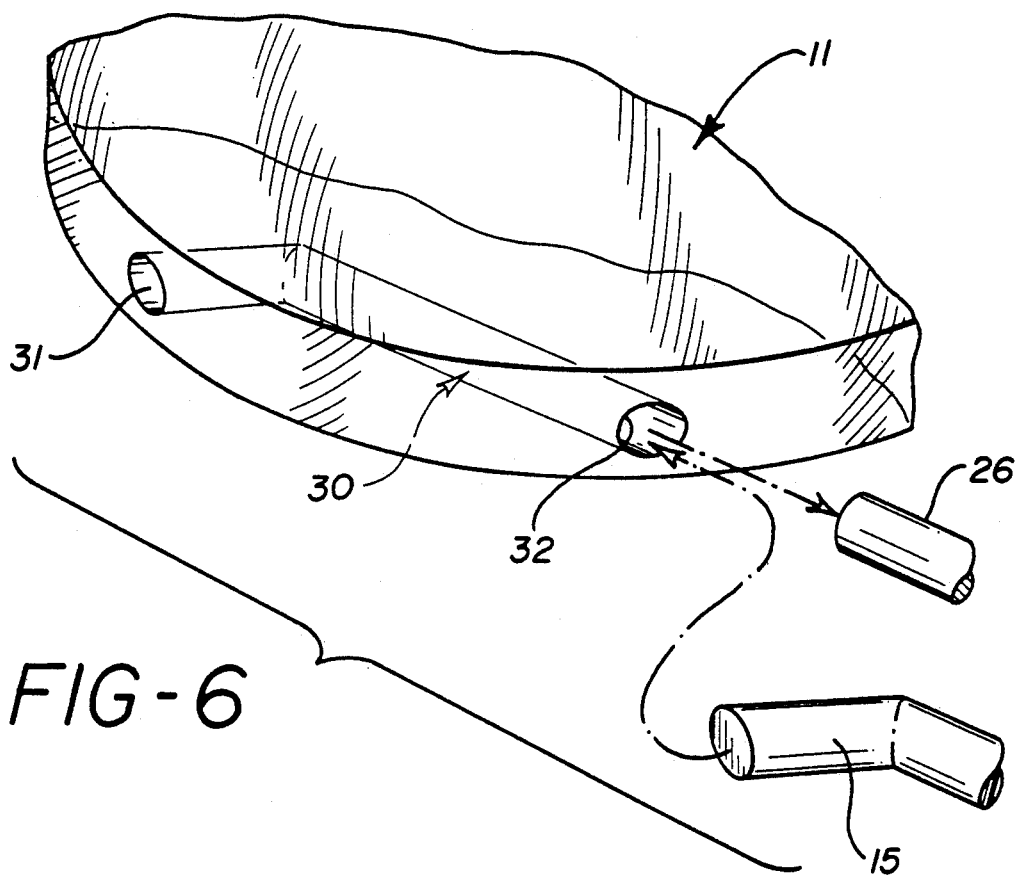
FIG-6
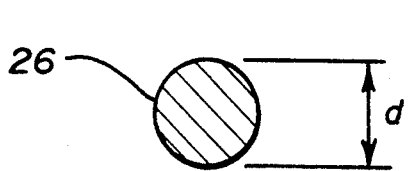
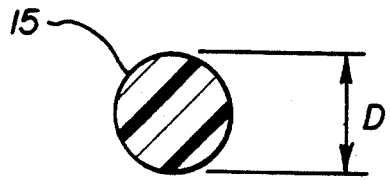
FIG-7   FIG-8

HAPTIC ATTACHMENT FOR SOFT INTRAOCULAR LENS

BACKGROUND OF THE INVENTION

This invention relates to a method of molding a deformable optic for a soft intraocular lens. More specifically, it relates to a method of molding such an optic which has an opening therein for securely receiving a haptic, which is the filamentary strand supporting the optic of the intraocular lens in the eye.

Flexible intraocular lenses which can be deformed to facilitate insertion through a small incision in the eye have steadily gained popularity in recent years. In contrast to conventional rigid intraocular lenses, for example, polymethylmethacrylate (PMMA) lenses, "soft" intraocular lenses offer advantages for ophthalmic surgeons with respect to the way in which the lens can be inserted in the eye. Since a soft intraocular lens can be folded or compressed to fit through a corneal incision having a diameter smaller than that of the soft lens in an undeformed condition, the patient receiving the intraocular lens will experience less surgical trauma and a shortened recovery period.

Although soft intraocular lenses have demonstrated numerous practical advantages for the ophthalmic surgeon, technological difficulties still remain for the preparation of these lenses. Scientists and engineers have continually worked on successfully attaching the haptic to the optic of the intraocular lens. The haptic supports the optic in the eye and therefore performs a necessary function for the successful operation of the lens. The traditional machining and staking processes for attaching the haptic to a rigid optic are inappropriate for soft optic attachment because of the flexible, deformable nature of the soft optic. Numerous attempts have been made to provide methods for securely fastening the haptic to a soft optic of an intraocular lens.

U.S. Pat. Nos. 4,880,426 and 4,894,062 disclose molding the material from which the deformable optic is derived about a portion of the haptic of the intraocular lens. That portion of the haptic which is embedded within the molded optic is configured in such a manner so as to securely attach the haptic to the optic. For example, the tip of the haptic embedded in the optic may be "balled" by applying heat to the tip to soften the haptic, or the haptic may be attached to an anchoring member which may be in the form of an arcuate filamentary strand or an elongated rod. U.S. Pat. No. 4,786,445 discloses the use of laser energy to attach the haptic to a soft optic of an intraocular lens.

Although the methods described above eliminate the need to use conventional means for attaching the haptic to the optic, these methods have their drawbacks. Foremost among the problems associated with these methods is that the portion of the haptic embedded in the optic is subjected to the curing temperature required to mold the material from which the soft optic is prepared. Unfortunately, the elevated temperature associated with the curing operation will cause the filamentary haptic strand to deform. This deformation may significantly affect the performance of the haptic for supporting the optic of the intraocular lens securely within the eye. It is most pronounced with haptics composed of the most commonly used materials, such as polypropylene and polymethylmethacrylate. These polymeric materials have softening temperatures which are below the temperatures required to cure the material from which the optic is made.

Therefore, in view of the deficiencies inherent in prior art methods for attaching a filamentary fixation member to a soft, deformable optic, a new method is needed for securely fastening a haptic to such an optic.

SUMMARY OF THE INVENTION

The invention is a method of molding a deformable optic for a soft intraocular lens. The optic has at least one opening therein for securely receiving a proximal end portion of a filamentary fixation member. The method comprises the sequential steps of positioning a wire-like insert member in a mold for the optic at a location corresponding to the desired location of the opening; filling the mold about the wire-like insert member with a curable material selected to form the deformable optic; curing the material so as to form the molded optic with the wire-like insert member embedded therein; and removing the wire-like insert member from the molded optic.

The method of this invention can be used to mold a deformable optic having an opening therein for securely receiving a filamentary fixation member, or "haptic", of an intraocular lens. Once the optic is formed with the opening, the haptic can be readily inserted into the opening for secure attachment of the haptic to the optic. In the preferred embodiment, the opening formed in the optic has a cross-sectional diameter smaller or substantially equal to that of the haptic. It is unnecessary to use the conventional staking or machining methods associated with rigid lenses for haptic attachment. More significantly, it is unnecessary to subject the haptic to the elevated temperature necessary for curing the material from which the optic is made. Therefore, it eliminates the disadvantage of deforming the haptic when the haptic is attached to the molded optic.

BRIEF DESCRIPTION OF THE DRAWINGS

FIG. 6 is a fragmentary perspective view showing a portion of a deformable optic made in accordance with the method of this invention.

FIG. 7 is a cross-sectional view of the wire-like insert member used to make the deformable optic in accordance with the method of this invention.

FIG. 8 is a cross-sectional view of the proximal end portion of a filamentary fixation member which can be used to prepare a soft intraocular lens from the deformable optic.

DESCRIPTION OF THE PREFERRED EMBODIMENT

Figure 1:
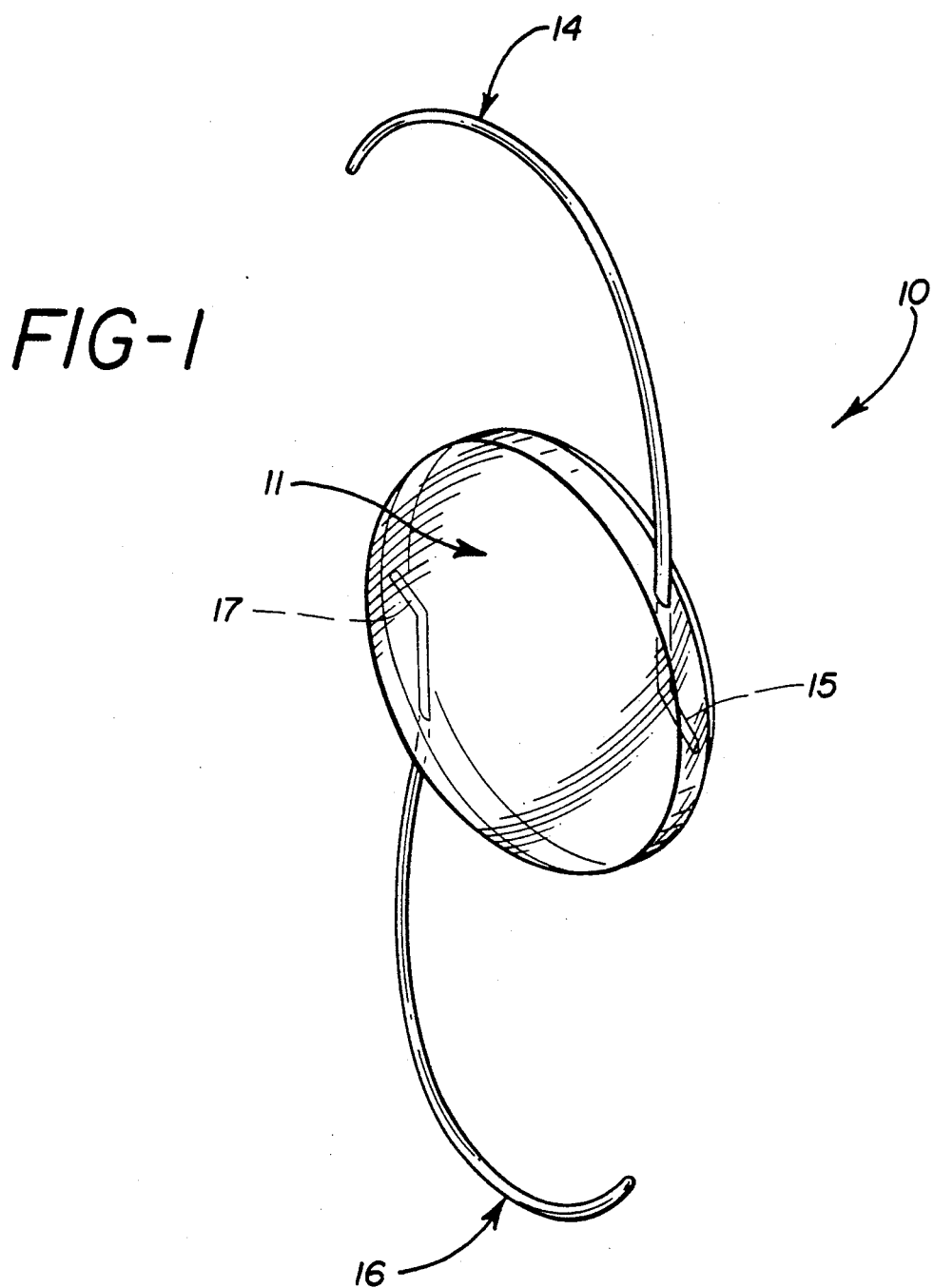
FIG. 1 is a perspective view of a soft intraocular lens which can be prepared from a deformable optic made in accordance with the teachings of the method of this invention.
Figure 2:
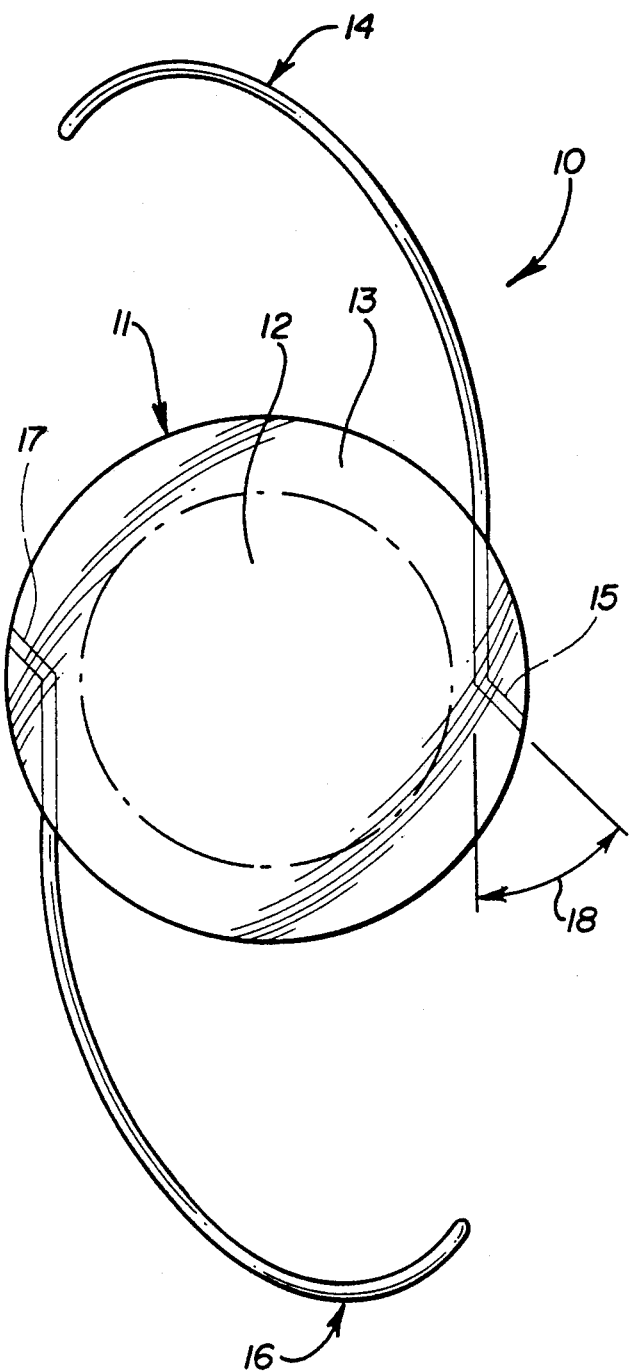
FIG. 2 is a front elevational view of the soft intraocular lens of FIG. 1.
Figure 3:
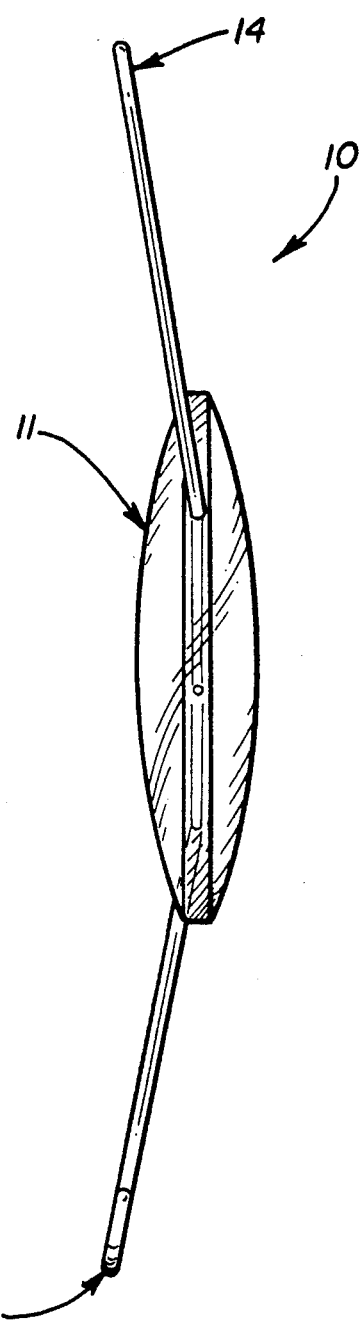
FIG. 3 is a right side elevational view of the soft intraocular lens of FIG. 2.

FIGS. 1-3 show a preferred soft intraocular lens ("IOL") made from a deformable optic in accordance with the method of this invention. IOL 10 has a deformable optic 11 with an optic zone 12 and a peripheral zone 13. The peripheral zone is not in the field of vision of the patient after the lens is implanted in the eye.

Deformable optic 11 can be made of any transparent, biocompatible material suitable for ophthalmic applications, provided the material can be "cured" to form the optic. The term "curable" is used in the broad sense to describe any material which can be processed in a practical manner to form the optic. Such materials include polymerizable monomers, regardless whether the monomer polymerizes to form a thermoplastic or thermoset. Ideally, the material is pourable so it can be poured into the mold to substantially fill the mold cavity easily and conveniently. Preferably, the optic is derived from a polymerizable monomer, especially from the polymerization of a silicone monomer.

Attached to the deformable optic of the IOL are filamentary fixation members 14 and 16, spaced about 180° apart from each other. The filamentary fixation members are attached at their respective proximal end portions 15 and 17. Preferably, the proximal end portions of the filamentary fixation members are embedded within the peripheral zone of the optic. As shown in FIG. 2, the proximal end portion of each filamentary fixation member preferably has a bend of approximately 45°. This bend is desired to increase resistance to movement, and therefore to increase the force necessary to remove the filamentary fixation member from the optic and to prevent the filamentary fixation member from rotating. To achieve this purpose, the bend angle only needs to be at least approximately 30°. The angle of the bend can be decreased or increased, and the optimum angle will depend on the composition of the optic and filamentary fixation members, as well as on the degree of resistance desired for any given application.

FIG. 3 illustrates the preferred biconvex structure of the circular optic, however any optical configuration suitable for an IOL is within the scope of this invention. For example, the shape of the optic can be not only circular but also oval, and the optic geometry can be in the form of a plano convex configuration.

The filamentary fixation members can be made of any biocompatible material which can be processed to fabricate the desired filamentary structure. Such materials include polypropylene, polymethylmethacrylate, certain polyamides and fluorocarbons such as polyvinylidene fluoride and other high temperature thermoplastics. The preferred material is polypropylene. The configuration of the filamentary fixation members can be in any form conventionally used for IOL design, but the preferred configuration is known as the modified J configuration shown in FIGS. 1-3.

The process of molding the curable material which forms the deformable optic about the wire-like insert member can be carried out using conventional cast molding techniques In fact, the process described in U.S. Pat. No. 4,978,354 for molding a soft IOL can be used to prepare the deformable optic made according to the invention, except the wire-like insert members are embedded in the mold cavity in place of the filamentary fixation members.

Figure 4:
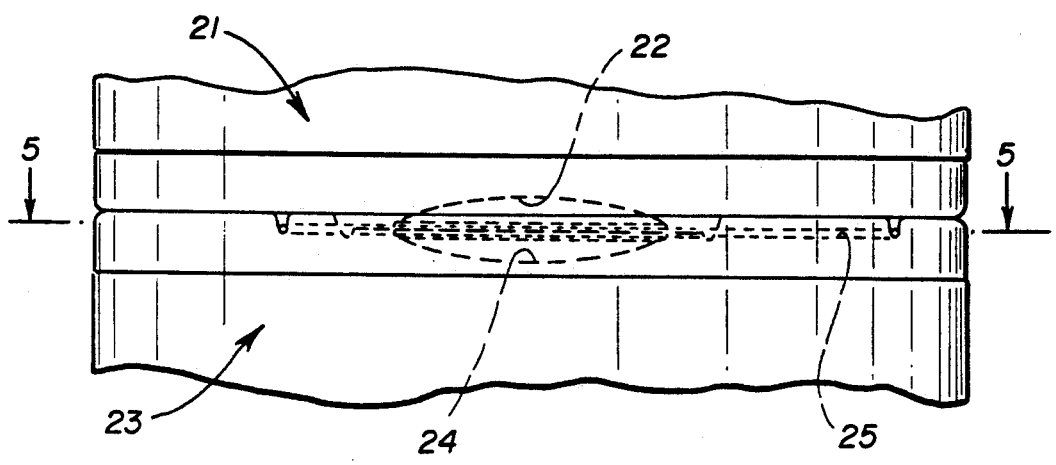
FIG. 4 is a partial side elevational view of a mold which can be used to prepare a deformable optic made in accordance with the method of this invention.
Figure 5:
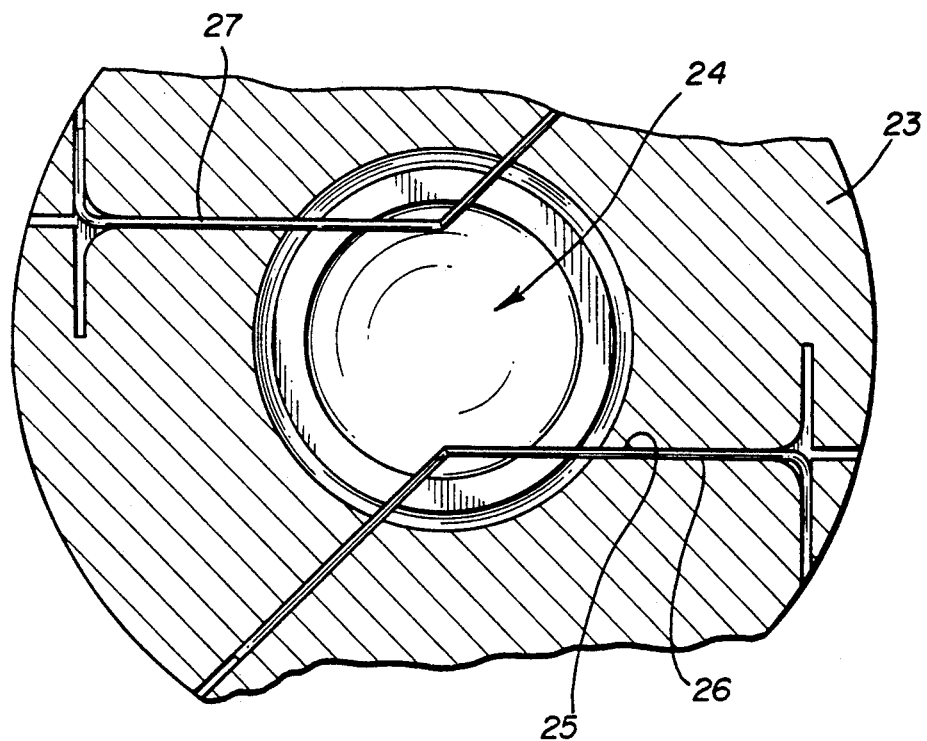
FIG. 5 is a cross-sectional view of the mold as taken along 5—5 of FIG. 4.

FIGS. 4 and 5 illustrate a conventional mold at 20 which can be used to prepare the deformable optic of this invention. The mold has a top mold half 21 with a desired mold cavity 22, and an opposing and complementary bottom mold half 23 with a bottom mold cavity 24. Channel 25 is for positioning a first wire-like insert member. As shown in more detail in FIG. 5, wire-like insert members 26 and 27 are positioned within their respective channels in the mold. The channels correspond to the desired configuration and location of the openings in the molded optic for securely receiving proximal end portions 15 and 17 of filamentary fixation members 14 and 16, respectively.

Once the wire-like insert members are properly positioned in their respective channels in the bottom mold half, the mold cavity is then filled with the selected curable material containing any other desired ingredients. The top mold half is mated and fastened to the bottom mold half. The curable composition is subsequently cured using conventional techniques of heat, pressure and time The wire-like insert member used in the method of this invention should have a softening temperature higher than that of the curable material, so that when such material is cured, it does not deform the wire-like insert member. The wire-like insert member preferably is composed of a material that exhibits low toxicity, is stable at processing temperatures, and is suitable for medical device applications. It should not be reactive with the curable material chosen to form the molded optic Furthermore, the wire-like insert member must be formable to any desired configuration. The preferred configuration is such that a portion of the wire-like insert member has a configuration substantially identical to that of the proximal end portion of the filamentary fixation members depicted in FIG. 2. The preferred wire-like insert members are stainless steel and polyaramide fibers. The most preferred wire-like insert member is a stainless steel wire.

The wire-like insert member preferably has a uniform cross-sectional diameter along its entire length, and only a portion of the wire-like insert member is positioned within the mold cavity. In this manner, it is easy to remove the wire-like insert member after the optic is molded by pulling on that portion of the wire-like insert member which was not positioned in the mold cavity.

After the optic material is cured, the mold halves are separated, any excess material is deflashed, and the molded optic with the wire-like insert members embedded therein is removed from the mold. As illustrated in FIG. 6, the wire-like insert member is removed from the molded optic, leaving behind the opening in the molded optic which conforms to the desired shape of the proximal end portion of the filamentary fixation members. In the preferred embodiment, the opening made from the removal of the wire-like insert member extends from a first peripheral edge position 31 to a second peripheral edge position 32 in a plane parallel to the plane of the optic.

Once the wire-like insert member is removed, proximal end portion 15 of the filamentary fixation member can be securely inserted into the opening 30 for final fabrication of the soft IOL. The filamentary fixation member can be pushed into the opening through peripheral edge position 32, and as the filamentary fixation member is pushed through the opening, any air which is entrapped in the opening can escape at peripheral edge position 31. If desired, once the proximal end portion of the filamentary fixation member is fully positioned in the opening of the optic, localized heat can be applied for a short time to optimize the ability of the proximal end portion of the filamentary fixation member to conform to the configuration of the opening, especially at the bend.

As illustrated in FIGS. 7 and 8, the proximal end portion of the filamentary fixation member desirably has a cross-sectional diameter, D, greater than the cross-sectional diameter of the wire-like insert member, d (although the invention can be used effectively when the diameters are substantially equal). Therefore, the diameter of the proximal end portion will be greater than the opening in the molded optic when the wire-like insert member is removed. The increased diameter of the proximal end portion of the filamentary fixation member serves to further increase the pull force necessary to remove the filamentary fixation member from the optic. It is possible for the proximal end portion of the filamentary fixation member to have a larger diameter than that of the opening of the deformable optic because as the filamentary fixation member is pushed into the opening, the opening expands to fit the diameter of the proximal end portion of the filamentary fixation member.

The invention has been described in its preferred embodiments. Numerous additional embodiments will become apparent to those skilled in this art, and such additional embodiments are well within the scope of the claimed invention.

What is claimed is:

1. A method of molding a deformable optic for a soft intraocular lens, wherein the optic has an opening therein for securely receiving a proximal end portion of a filamentary fixation member, comprising the sequential steps of:
   a) positioning an insert member having a cross-sectional diameter smaller than that of the proximal end portion of the filamentary fixation member in a mold for the optic at a location corresponding to the desired location of the opening.
   b) filling the mold about the insert member with a curable material selected to form the deformable optic,
   c) curing the material so as to form the molded optic with the insert member embedded therein,
   c) removing the insert member from the molded optic so as to form an opening to receive the proximal end portion of the filamentary fixation member, and
   d) expanding said opening by insertion of said proximal end portion of the filamentary fixation member into said opening.

2. The method of claim 1 wherein the insert member is stainless steel wire.

3. The method of claim 2 wherein the stainless steel wire has a uniform cross-sectional diameter.

4. The method of claim 3 wherein only a portion of the stainless steel wire is embedded in the molded optic.

5. The method of claim 4 wherein the stainless steel wire is embedded at or near the periphery of the molded optic outside the optic zone.

6. The method of claim 5 wherein the stainless steel wire is embedded within a plane parallel to the plane of the optic.

7. The method of claim 6 wherein the portion of the stainless steel wire embedded in the molded optic has a bend of at least about 30°.

8. The method of claim 7 wherein the portion of the stainless steel wire embedded in the molded optic has a bend of at least about 45°.

9. The method of claim 8 wherein the stainless steel wire embedded in the molded optic extends from a first peripheral edge position to a second peripheral edge position.

10. The method of claim 9 wherein the molded optic has a second opening therein for securely receiving a proximal end portion of a second filamentary fixation member, said second opening spaced about 180° apart from the first opening and having substantially an identical configuration to that of the first opening.

11. The method of claim 10 wherein the curable material is a polymerizable monomer.

12. The method of claim 11 wherein the polymerizable monomer is a silicone monomer.

13. The method of claim 12 further comprising the step of inserting the proximal end portion of the first filamentary fixation member in the first opening and the proximal end portion of the second filamentary fixation member in the second opening so as to prepare the soft intraocular lens.

* * * * *